United States Patent [19]
Mayo

[11] Patent Number: 5,955,577
[45] Date of Patent: Sep. 21, 1999

[54] METHOD FOR SYNTHESIZING A WATER-SOLUBLE β-SHEET FORMING PEPTIDE

[75] Inventor: Kevin H. Mayo, Minnetonka, Minn.

[73] Assignee: Regents of the University of Minnesota

[21] Appl. No.: 08/671,487

[22] Filed: Jun. 27, 1996

[51] Int. Cl.[6] .................................................. A61K 38/00
[52] U.S. Cl. ......................... 530/333; 530/334; 530/335; 530/338
[58] Field of Search .................................. 530/324–330, 530/333–339

[56] References Cited

U.S. PATENT DOCUMENTS 5,190,873  3/1993  Lernhardt et al. ...................... 435/177
5,786,324  7/1998  Gray et al. .

FOREIGN PATENT DOCUMENTS

WO 92/09695  6/1992  WIPO ............................. C12N 15/62
WO 96/31528  10/1996  WIPO ............................. C07K 7/06
WO 96/37212  11/1996  WIPO ............................. A61K 38/00

OTHER PUBLICATIONS

Ilyina et al., "Multiple native–like conformations trapped via self–association–induced hydrophobic collapse of the 33–residue β–sheet domain from platelet factor 4," *Biochem. J.*, 306, 407–419 (1995).

Ilyina et al., "NMR Structure of a de Novo Designed, Peptide 33mer with Two Distinct, Compact β–Sheet Folds," *Biochemstry*, 36, 5245–5250 (1997).

Miller et al., "Biology and Biochemistry of the Chemokines: A Family of Chemotactic and Inflammatory Cytokines," *Critical Reviews in Immunology*, 12(1,2), 17–46 (1992).

R. J. Battafarano et al., "Peptide derivatives of three distinct lipopolysaccharide–induced tumor necrosis factor–alpha secretion in vitro," *Surgery*, 118(2), 318–324 (Aug. 1995).

A.S. Altieri et al., "Association of Biomolecular Systems via Pulsed Field Gradient NMR Self–Diffusion Measurements", *J. Am. Chem. Soc.*, 117 7566–7567 (1995).

A. Anisowicz et al., "Constitutive overexpression of a growth–regulated gene in transformed Chinese hamster and human cells", *Proc. Natl. Acad. Sci. USA*, 84 7188–7192 (1987).

A. Bax et al., "MLEV–17–Based Two–Dimensional Homonuclear Magnetization Transfer Spectroscopy", *J. Magnetic Resonance*, 65 355–360 (1985).

Cantor et al., "The behavior of biological macromolecules", *Biophysical Chemistry*, Part III 979–1039 (1980).

T.F. Deuel et al., "Amino acid sequence of human platelet factor 4", *Proc. Natl. Acad. Sci. USA*, 74 2256–2258 (1977).

S.J. Gibbs et al., "A PFG NMR Experiment for Accurate Diffusion and Flow Studies in the Presence of Eddy Currents", *J. Magnetic Resonance*, 93 395–402 (1991).

E.F. Hartree, "Determination of Protein: A Modification of the Lowry Method That Gives a Linear Photometric Response", *Analytical Biochem.*, 48 422–427 (1972).

J.C. Holt et al., "Biochemistry of α Granule Proteins", *Seminars in Hematology*, 22 151–163 (1985).

(List continued on next page.)

*Primary Examiner*—Jeffrey Stucker
*Attorney, Agent, or Firm*—Mueting, Raasch & Gebhardt, P.A.

[57] ABSTRACT

A method for synthesizing a water-soluble β-sheet forming peptide having at least about 35% amino acids having hydrophobic side chains, the method comprising linking amino acids having charged side chains and amino acids having noncharged polar side chains with amino acids having hydrophobic side chains, wherein the amino acids having charged side chains are provided in a ratio of at least about 2:1 amino acids having positively charged side chains to amino acids having negatively charged side chains; wherein the peptide is water soluble under physiological conditions and forms β-sheet structures.

15 Claims, 4 Drawing Sheets

Native α-Chemokine Sequences.

```
PF4    R H I T S L E V I K A G P H S P T A Q L I A T L K N G R K I S L D
                 25        30         35          40      45          50
IL-8   K F I K E L R V I E S G P H S A N T E I I V K L S D G R E L S L D

GRO    K N I Q S V N V K S P G P H S A Q T E V I A T L K N G R K A S L N
```

Designed Peptides.

OTHER PUBLICATIONS

E. Ilyina et al., "Synthetic Peptides Probe Folding Initiation Sites in Platelet Factor–4: Stable Chain Reversal Found within the Hydrophobic Sequence LIATLKNGRKISL", *Biochemistry*, 33 13436–13444 (1994).

J. Jeener, "Investigation of exchange processes by two–dimensional NMR spectroscopy", *J. Chem. Phys.*, 71 4546–4553 (1979).

C.A. Kim et al., "Thermodynamic β–sheet propensities measured using a zinc–finger host peptide", *Nature*, 362 267–270 (1993).

D. Marion et al., "Application of Phase Sensitive Two–Dimensional Correlated Spectroscopy (COSY) for Measurements of $^1$H–$^1$H Spin–Spin Coupling Constants in Proteins", *Biochemical and Biophysical Research Communications*, 113 967–974 (1983).

D.L. Minor et al., "Context is a major determinant of β–sheet propensity", *Nature*, 371 264–267 (1994).

D.L. Minor et al., "Measurement of the β–sheet–forming propensities of amino acids", *Nature*, 367 660–663 (1994).

D.E. Otzen et al., "Side–Chain Determinants of β–Sheet Stability", *Biochemistry*, 34 5118–5124 (1995).

U. Piantini et al., "Multiple Quantum Filters for Elucidating NMR Coupling Networks", *J. Am. Chem. Soc.*, 104 6800–6801 (1982), T.P. Quinn et al., "Betadoublet: De novo design, synthesis, and characterization of a β–sandwich protein", *Proc. Natl. Acad. Sci. USA*, 91 8747–8751 (1994).

J.S. Richardson et al., "Looking at proteins: representations, folding, packing, and design", *Biophysical Journal*, 63 1186–1209 (1992).

C.K. Smith et al., "A Thermodynamic Scale for the β–Sheet Forming Tendencies of the Amino Acids", *Biochemistry*, 33 5510–5517 (1994).

D.J. States et al., "A Two–Dimensional Nuclear Overhauser Experiment with Pure Absorption Phase in Four Quadrants", *J. Magnetic Resonance*, 48 286–292 (1982).

Stewart et al., *Solid phase peptide synthesis*, 2nd ed. Rockford, Illinois, Pierce Chemical Co. pp. 125–135 (1984).

P.R. Wills et al., "Concentration Dependence of the Diffusion Coefficient of a Dimerizing Protein: Bovine Pancreatic Trypsin Inhibitor", *J. Phys. Chem.*, 85 3978–3984 (1981).

G. Wider et al., "Homonuclear Two–Dimensional $^1$H NMR of Proteins. Experimental Procedures", *J. Magnetic Resonance*, 56 207–234 (1984).

Y. Yan et al., "Engineering of betabellin 14D: Disulfide–induced folding of a β–sheet protein", *Protein Science*, 3 1069–1073 (1994).

Native α-Chemokine Sequences.

PF4  R H I T S L E V I K A G P H S P T A Q L I A T L K N G R K I S L D
              25              30              35              40              45              50

IL-8  K F I K E L R V I E S G P H S A N T E I I V K L S D G R E L S L D

GRO  K N I Q S V N V K S P G P H S A Q T E V I A T L K N G R K A S L N

Designed Peptides.

Fig. 1

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 33 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Lys Phe Ile Val Thr Leu Arg Val Ile Lys Ala Gly Pro His Ser Pro
1               5                   10                  15

Thr Ala Gln Ile Ile Val Glu Leu Lys Asn Gly Arg Lys Leu Ser Leu
            20                  25                  30

Asp (2) INFORMATION FOR SEQ ID NO:2:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Ala Asn Ile Lys Leu Ser Val Glu Met Lys Leu Phe Lys Arg His Leu
 1               5                  10                  15

Lys Trp Lys Ile Ile Val Lys Leu Asn Asp Gly Arg Glu Leu Ser Leu
            20                  25                  30

Asp
```

(2) INFORMATION FOR SEQ ID NO:3:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Ala Asn Ile Lys Leu Ser Val Glu Met Lys Leu Phe Cys Tyr Trp Lys
 1               5                  10                  15

Val Cys Lys Ile Ile Val Lys Leu Asn Asp Gly Arg Glu Leu Ser Leu
            20                  25                  30

Asp
```

(2) INFORMATION FOR SEQ ID NO:4:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ser Ile Gln Asp Leu Asn Val Ser Met Lys Leu Phe Arg Lys Gln Ala
 1               5                  10                  15

Lys Trp Lys Ile Ile Val Lys Leu Asn Asp Gly Arg Glu Leu Ser Leu
            20                  25                  30

Asp
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Leu Xaa Xaa Gly Arg
 1               5
```

```
(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Lys Xaa Xaa Gly Arg
    1               5

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ile Ile Val Lys Leu Ser Asp Gly Arg Glu Leu Ser Leu
    1               5                  10

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Tyr Trp Lys Val
```

METHOD FOR SYNTHESIZING A WATER-SOLUBLE β-SHEET FORMING PEPTIDE

FIELD OF THE INVENTION

This invention relates to the fields of chemical design and to methods for selecting, modifying, and creating synthetic chemical structures.

BACKGROUND

A critical feature of a polypeptide is its ability to fold into a three dimensional conformation or structure. Polypeptides usually have a unique conformation which, in turn, determines their function. The conformation of a polypeptide has several levels of structure. The primary structure is a linear sequence of a series of amino acids linked into a polypeptide chain. The secondary structure describes the path that the polypeptide backbone of the polypeptide follows in space, and the tertiary structure describes the three dimensional organization of all the atoms in the polypeptide chain, including the side groups as well as the polypeptide backbone.

Covalent and noncovalent interactions between amino acids determine the conformation of a polypeptide. The most common covalent bond used in establishing the secondary and tertiary structure of a polypeptide is the formation of disulfide bridges between two cysteine residues (forming cystine). The formation of noncovalent bonds is influenced by the aqueous environment such as water. A large number of noncovalent interactions, such as van der Waals, ionic, hydrophobic and hydrogen-bonded interactions, contribute to the way in which a polypeptide folds. Hydrophobic interactions, which occur between amino acids with nonpolar side chains, are particularly important because they associate to exclude water. These side chains generally form the core of the polypeptide, where they are mostly inaccessible to water.

The secondary structure of polypeptides can be divided into two general classes: α-helix and β-sheet. An α-helix is stabilized by hydrogen bonding and side chain interactions between amino acids three and four residues apart in the same polypeptide chain, whereas a β-sheet is stabilized by hydrogen bonding and side chain interactions between amino acids more distant in a polypeptide chain and in different polypeptide chains. A complete understanding of the construction of α helices and β sheets is important for the manipulation of the structure and function of polypeptides.

A major challenge in de novo polypeptide design (more often referred to as de novo peptide design), which is the design of polypeptides (or peptides) from scratch, is the engineering of a polypeptide having the folding stability of the native structure of a natural polypeptide. Several polypeptides have been designed with the α helix as the major structural element. Few polypeptideshave been designed with the β sheet as the major structural element. Unlike α helices where there is a regular succession of hydrogen bonds between amides three and four residues apart in the sequence, β sheets are formed by residues at variable and often distant positions in the sequence. In addition, they tend to form aggregates in solution and precipitate under physiological conditions. A major difficulty in designing a structurally stable β polypeptide is dealing with the interactions between β sheets.

Designing a polypeptide to form a β-sheet has in the past usually been based on one of a number of structural propensity scales known in the art. These scales are derived either statistically from structural databases of known folded polypeptides or by making single or minimal site-specific changes in a fully folded polypeptide. See, for example, C. A. Kim, et al., Nature, 362, 267 (1993); D. L. Minor, et al., Nature, 371, 264 (1994); D. L. Minor, et al., Nature, 367, 660 (1994); and C. K. Smith, et al., Biochemistry, 33, 5510 (1994). However, such scales are generally less useful when designing de novo β-sheet folds in short peptides where considerably more β-sheet and/or side-chain surface (particularly hydrophobic surface) will be exposed to water. D. E. Otzen, et al., Biochemistry, 34, 5718 (1995).

Betabellin was one of the first de novo designed class of β-sheet peptides. J. Richardson, et al., Biophys. J., 63, 1186 (1992). It was intended to fold into a sandwich of two identical four-stranded, antiparallel β sheets. A more recent version of betabellin, betabellin 14D, was designed by Yan, et al., Protein Science, 3, 1069, (1994). Quinn, et al. designed betadoublet, which is similar to betabellin but contains only naturally encoded amino acids. T. P. Quinn, et al., Proc. Natl. Acad. Sci. U.S.A., 91, 8747 (1994).

However, peptides in the betabellin and betadoublet series show limited solubility in water and minimal, highly transient β-sheet structure, i.e., nonstable structures. The best betabellin made thus far, Betabellin peptide 14D, for example, becomes less soluble at pH values above 5.5 making it impractical for use at a physiological pH. Moreover the β-sheet structure formed by peptide 14D relies on the presence of an intermolecular disulfide bridge to yield a dimeric species. The peptides of the present invention do not have these limitations. Betadoublet, which has the same predicted antiparallel β-sheet motif as betabellin, is even less water soluble, and only at a lower pH of about 4, and fails to show any compact, stable folding, i.e., structure.

Water solubility and pH ranges are important to peptide function. A polypeptide that is not soluble under physiological conditions (i.e., in water at a pH of about 7.0–7.4 and in about 150 mM NaCl or an equivalent physiological salt) is not functional and is therefore not useful. Neither the betabellin nor the betadoublet strategies for peptide design achieved sufficient solubility, peptide compactness, or peptide self-association under physiological conditions.

Hence, there remains a need for β-sheet forming peptides that are not only water soluble, but soluble at physiological conditions, and self associate.

SUMMARY OF THE INVENTION

The present invention provides a method for synthesizing a water-soluble peptide having at least about 35% amino acids having hydrophobic side chains, the method comprising combining amino acids having charged side chains and amino acids having noncharged polar side chains with amino acids having hydrophobic side chains, wherein the amino acids having charged side chains are provided in a ratio of at least about 2:1 amino acids having positively charged side chains to amino acids having negatively charged side chains.

The present invention also provides a method for synthesizing a water-soluble peptide having at least about 35% amino acids having hydrophobic side chains, the method comprising combining amino acids having charged side chains and less than about 20% amino acids having noncharged polar side chains with amino acids having hydrophobic side chains, wherein: the amino acids having charged side chains are provided in a ratio of at least about 2:1 amino acids having positively charged side chains to amino acids having negatively charged side chains;the water-soluble peptide has about 35% to about 55% amino acids having hydrophobic side chains; and at least two of the amino acids having hydrophobic side chains are positioned in the peptide with an intervening turn sequence in a manner such that the two amino acids having hydrophobic side chains are capable of aligning in a pairwise fashion to form a β-sheet structure; and the turn sequence is LXXGR, (SEQ ID NO:5) wherein each X is independently selected from the group consisting of K, N, S, and D. Herein, percentages are reported as the number of specified amino acids relative to the total number of amino acids in the peptide chain.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted. One letter and three letter symbols are used herein to designate the naturally occurring amino acids. Such designations including R or Arg, for Arginine, K or Lys, for Lysine, G or Gly, for Glycine, and X for an undetermined amino acid, and the like, are well known to those skilled in the art.

The term "peptide" or "polypeptide" is used herein to refer to an amino acid polymer. A single peptide of this invention preferably has at least 20 amino acids. Preferably the peptides of this invention are no greater than 50 amino acids in length, and more preferably about 28 to about 33 amino acids in length.

The term "water-soluble" is used herein to refer to compounds, molecules, and the like, including the peptides of this invention, that are preferably readily dissolved in water. The compounds of this invention are readily dissolved in water if about 1 mg of the compound dissolves in 1 ml of water having a temperature of about 35–45° C. More preferably, the peptides of this invention will have a water solubility of at least about 10 mg/ml and often of at least about 20 mg/ml. Even more preferably, the peptides are soluble at these concentrations under physiological conditions, including a pH of about 7.0–7.4 and a salt concentration of about 150 mM NaCl.

The term "hydrophobic amino acid side chain" or "nonpolar amino acid side chain," is used herein to refer to amino acid side chains having properties similar to oil or wax in that they repel water. In water, these amino acid side chains interact with one another to generate a nonaqueous environment. Examples of amino acids with hydrophobic side chains include, but are not limited to, valine, leucine, isoleucine, phenylalanine, and tyrosine.

The term "polar amino acid side chain" is used herein to refer to groups that attract water or are readily soluble in water or form hydrogen bonds in water. Examples of polar amino acid side chains include hydroxyl, amine, guanidinium, amide, and carboxylate groups. Polar amino acid side chains can be charged or noncharged.

The term "noncharged polar amino acid side chain" or "neutral polar amino acid side chain" is used herein to refer to amino acid side chains that are not ionizable or do not carry an overall positive or negative charge. Examples of amino acids with noncharged polar or neutral polar side chains includes serine, threonine, glutamine, and the like.

The term "positively charged amino acid side chain" refers to amino acid side chains that are able to carry a full or positive charge and the term "negatively charged amino acid side chain" refers to amino acid side chains that are able to carry a negative charge. Examples of amino acids with positively charged side chains include arginine, histadine, lysine, and the like. Examples of amino acids with negatively charged side chains include aspartic acid and glutamic acid, and the like.

The term "self-association" refers to the spontaneous association of two or more individual peptide chains or molecules irrespective of whether or not the peptide chains are identical.

BRIEF DESCRIPTION OF THE FIGURES

FIG. 1 provides the alignment of β-sheet regions from the polypeptides PF4, IL-8 and GRO polypeptides. β-sheet residues are blocked-in and lines connect the residues that are paired in the chain. The C-termini in the sequences were synthesized in the amide form. Numbering shown below the PF4 sequence is that from native PF4.

DETAILED DESCRIPTON OF THE INVENTION

Figure 2:
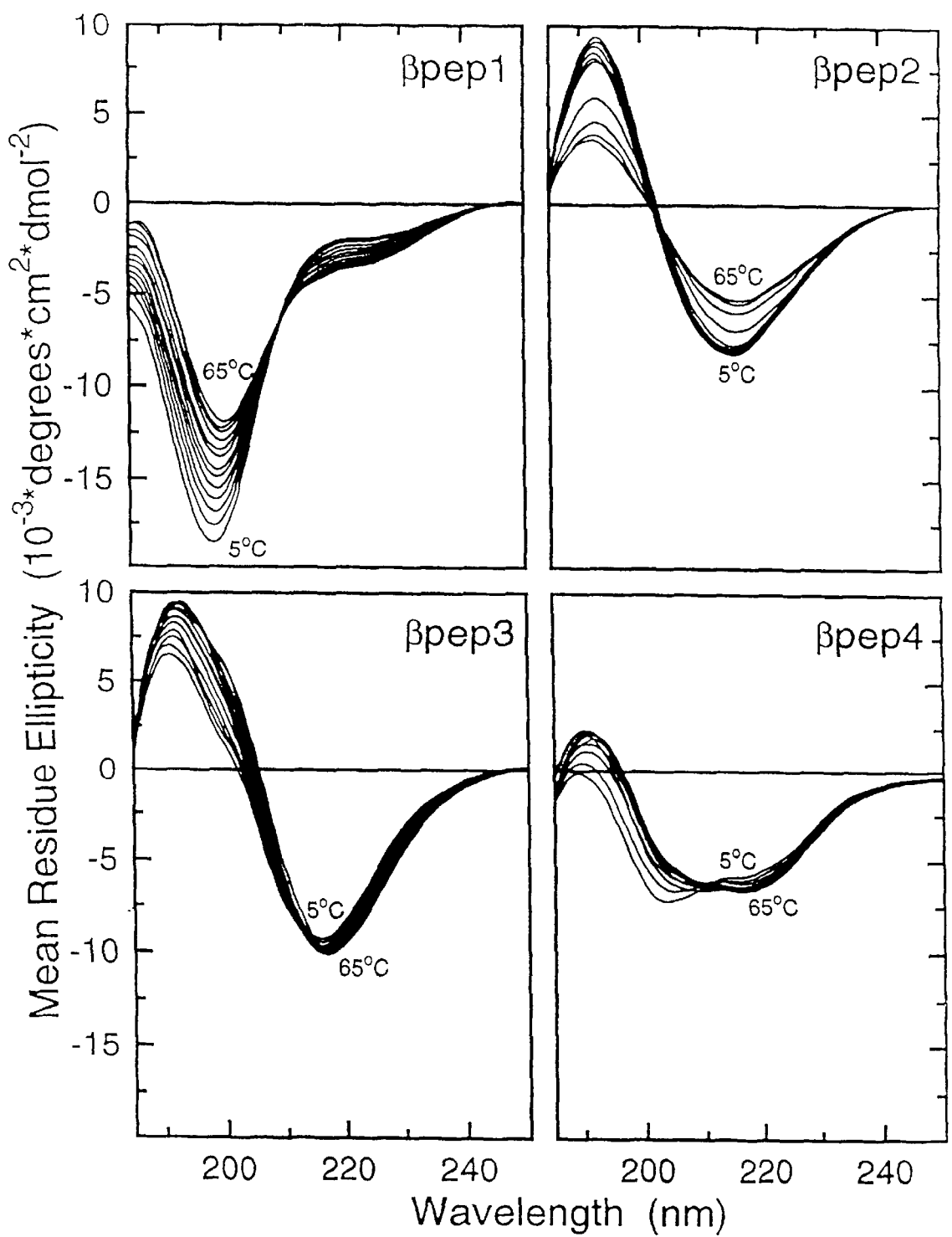
FIG. 2 is a graph illustrating the far-ultraviolet circular dichroic spectra for designed peptides βpep-1, βpep-2, βpep-3 and βpep4. Peptide concentration used was 10 to 20 μM in 20 mM potassium phosphate, pH=6.3. The temperature was varied from 5° C. to 75° C.

An intricate interplay exists between peptide β-sheet formation, self-association, and water solubility. A challenge in making a soluble folded peptide is that solubility has a double-edged effect: precipitation versus over-solvation. Precipitation is the falling out of solution of a peptide, while over-solvation is the tendency of a soluble peptide to prefer intermolecular water-peptide interactions over intramolecular folding interactions. Going too far in either direction (precipitation or over-solvation) destabilizes the folded state. Reduced solubility generally occurs due to intermolecular peptide-to-peptide interactions (hydrophobic and electrostatic) which results in precipitation or gelation. Although the precipitate, for example, is in equilibrium with soluble peptide, the equilibrium is shifted away from solution. If a designed β-sheet-forming peptide contains a relatively large number of amino acids with hydrophobic side chains which are not screened to some extent by the folding process, precipitation or gelation may result. Inherent in the design of β-sheet forming peptides, therefore, is the capacity to self-associate, thereby screening hydrophobic surface from solvent water.

The present invention provides a method for the de novo design of peptides that are water soluble at or near physiological conditions and preferably form β-sheet structures. Preferably and advantageously, the water-soluble peptide forms, through self-association, a β-sheet in the absence of any intermolecular covalent interactions (although this is not necessarily a requirement). The method takes into account the following parameters: the number or percentage composition of amino acids with positively and negatively charged side chains, the number or percentage composition of amino acids with noncharged polar side chains, the number or percentage composition of amino acids with hydrophobic side chains, proper placement and pairing of amino acids in the sequence and in space, and specific turn character. The specific turn character refers to the composition of side chains of the amino acids positioned in the turn sequence. A turn sequence refers to a sequence of amino acids that reverses the direction of the amino acid sequence in space.

When the number of amino acids with positively and negatively charged side chains is about equal, intermolecular electrostatic interactions shift the solvation-precipitation equilibrium to the precipitate state. This was a fundamental flaw in previous design approaches. Adjusting the overall net charge of the peptide to mostly amino acids with positively charged side chains greatly improves solubility. Inter-peptide charge repulsion may also help to reduce precipitation. In a preferred embodiment of this invention, the ratio of amino acids with positively charged side chains to amino acids with negatively charged side chains is at least about 2:1. Preferably the ratio of amino acids with positively charged side chains to amino acids with negatively charged side chains is no greater than about 3:1; however, this invention also considers larger ratios of amino acids with positively charged side chains to amino acids with negatively charged side chains including, but not limited to 4:1, 5:1, 6:1 or greater.

The other side to solubility is that a peptide can be too soluble, i.e., over-solvated. When the number of amino acids with polar side chains is too high and other stabilizing forces are too low, intramolecular collapse or folding may be opposed by intermolecular peptide-water associations. Therefore, a high content of amino acids with short chain polar side chains such as serine and threonine (the hydroxylated amino acids) is not desirable, even though threonine is at the top of β-sheet propensity scales. This was another fundamental flaw in previous design approaches. The peptides of the present invention preferably contain less than 100%, preferably less than about 50%, more preferably, less than about 20% amino acids with noncharged polar side chains.

An appropriate percent composition of amino acids with hydrophobic side chains and proper placement in the sequence of such amino acids promotes self-association-induced structural collapse and stability. The trade-off is to adjust the percent composition of amino acids with hydrophobic side chains to avoid insolubility, while promoting folding and structure formation. The peptides of this invention preferably contain about 35% to about 55% amino acids with hydrophobic side chains, and in particularly preferred embodiments, about 40% to about 50% amino acids with hydrophobic side chains. In preferred embodiments of this invention, the hydrophobic amino acids are aliphatic, although aromatic hydrophobic amino acids are also possible.

To generate a more compact fold, side-chain pairing and packing must be optimized. Hydrophobic interactions increase folded state stability. Choosing the proper placement of amino acids with hydrophobic side chains in the sequence and combination of hydrophobic side-chain triplets across the strands as well as between strands in the self-associated peptide is an important feature to designing stable β-sheet folds. As used herein, a strand is that portion of a folded peptide chain between turn sequences.

Preferably, the amino acids are spacially positioned in the folded peptide to form a substantially hydrophobic surface. More preferably, the amino acids are spacially positioned in the folded peptide such that one peptide molecule is capable of self-associating with another peptide molecule to form a multimer.

The added dimension to this β-sheet design process is oligomerization where efficient hydrophobic side-chain packing of one sheet on top of another appears to be important for optimum folding stability and compactness. Choosing the proper placement of side chains, particularly hydrophobic side chains, in the amino acid sequence is important to controlling fold stability. Compact β-sheet folding is typically dependent on well-packed inter-strand side chain pairings. In a preferred embodiment of this invention at least two amino acids with hydrophobic side chains, and more preferably, three amino acids with hydrophobic side chains are positioned to align in space to form a β-sheet structure. Between these amino acids are turn sequences to allow for these side chain pairings.

Specific turn character may promote or stabilize a desired fold. A variety of turn sequences are known in the art. For a particular β-sheet fold, some turns may be important, while others may not. Those skilled in the art will be able to incorporate a turn sequence into the peptides designed according to the methods of this invention to test whether or not the peptide maintains a β-sheet structure, and the like, following the methods provided in the Examples that follow. A specific novel folding initiation turn/loop sequence, KXXGR (SEQ ID NO:6) (Ilyina et al., Biochemistry 33, 13436 (1994) was used in SEQ ID NOS:1–4, as described in the Example section of this disclosure. In this sequence, each X is independently selected from the group consisting of K, N, S, and D. This sequence was positioned between two amino acids with hydrophobic side chains such that the two amino acids having hydrophobic side chains were capable of aligning in a pairwise fashion to form a β-sheet structure.

Using the invention disclosed herein, four peptides, βpep-1, βpep-2, βpep-3 and βpep4 (SEQ ID NOS: 1–4, respectively), were designed de novo. All four βpep peptides are water soluble at least up to 30 mg/mL (9 mM) at pH values between pH=2 and pH=10, and all form β-sheets. Three of the four de novo designed peptides, βpep-2, βpep-3 and βpep4, have been shown by circular dichoism (CD) and nuclear magnetic resonance (NMR) to form significant populations of self-association-induced β-sheet structure in water at near-physiological conditions. βpep4, in particular, exemplifies an exceptional application of this design approach by showing relatively stable, compact triple-stranded β-sheet structure with good side-chain packing in a tetrameric state.

Using the methods of this invention it is possible to create any number of peptides, preferably peptides having β-sheet structure. This invention provides a method for designing a peptide scaffold to support a peptide in its native β-sheet structure. Those skilled in the art will recognize that there are a variety of proteins and polypeptides with β-sheet structures and that many of the proteins and polypeptides containing these β-sheet structures are known to mediate, promote or inhibit a variety of biological effects.

For example, a number of biological effects have been mapped to peptide sequences in a protein that exhibit β-sheet conformations. This invention permits the selection of a peptide sequence from a protein in a domain having β-sheet structure and the incorporation of this peptide sequence into a scaffold, according to this invention, to create a peptide with retained β-sheet structure. These novel peptides can have the same or improved biological activity that is attributed to the peptide domain while in the native protein with the advantage that the remaining portions of the protein are not required for activity. The use of an entire protein to duplicate the effect of a peptide domain complicates experimentation and therapy. Other domains in a protein may stimulate other biological and chemical effects including, but not limited to, enhanced antigenicity, decreased solubility, or stimulate unwanted biological responses, and the like. The protein is often labile or is not suited for biological or therapeutic applications without further modification. The strategy of this invention permits a functional peptide domain to be retained in its tertiary conformation within the scaffold of this invention. The methods of this invention provide direction for those skilled in the art to generate a variety of peptides with novel activities or with activities attributable to a parent protein from which the peptide was originally derived.

Exemplary peptides (β-pep1–4, SEQ ID NOS:1–4 respectively) were prepared according to Example 1 and tested for their ability to neutralize endotoxin according to the methods of Example 5. The peptides demonstrated endotoxin neutralizing activity as compared to PF4 and had improved activity as compared to an equivalent region from protein B/PI (amino acids 86–108). Domains within amino acids 86–108 of B/PI have been shown to have endotoxin neutralizing activity. These results indicated that the peptides had biological activity.

The invention will be further described by reference to the following detailed examples. These examples are offered to further illustrate the various specific and preferred embodiments and techniques. It should be understood, however, that many variations and modifications may be made while remaining within the scope of the present invention.

EXAMPLE 1

The Design and Synthesis of Water-Soluble β-Sheet Forming Peptides

Peptides of 33 amino acid residues in length, called βpep-1, βpep-2, βpep-3 and βpep4, were synthesized on a Milligen Biosearch 9600 automated peptide synthesizer. The procedures used were based on Merrifield solid phase synthesis utilizing Fmoc-BOP chemistry (Stewart et al., 1984. *Solid phase peptide synthesis.,* 2nd ed. Rockford, Ill., Pierce Chemical Co. pp 125–135). After the sequence had been obtained, the peptide support and side chain protection groups were acid cleaved (trifluoroacetic acid and scavanger mixture). Crude peptides were analyzed for purity on a Hewlett-Packard 1090M analytical HPLC using a reverse phase C18 VyDac column. Peptides generally were about 90% pure. Further purification was done on a preparative reverse-phase HPLC C-18 column using an elution gradient of 0–60% acetonitrile with 0.1% trifluoroacetic acid in water. Peptides then were analyzed for amino acid composition on a Beckman 6300 amino acid analyzer by total hydrolysis of samples using 6N HCl at 110° C. for 18–20 hrs. N-terminal sequencing confirmed peptide purity. The amino acid sequences and compositions of the four peptides are given in Table 1, and the composition of the peptides is provided in Table 2. βpep-3 contains an amino acid in the D configuration as represented by the superscripted D.

TABLE 1

| Amino Acid Sequence of β-Peptides |
|---|
| β pep-1 (SEQ ID NO:1)<br>KFIVTLRVIKAGPHSPTAQIIVELKNGRKLSLD |
| β pep-2 (SEQ ID NO:2)<br>ANIKLSVEMKLFKRHLKWKIIVKLNDGRELSLD |
| β pep-3 (SEQ ID NO:3)<br>ANIKLSVEMKLFCY$^D$WKVCKIIVKLNDGRELSLD |
| β pep-4 (SEQ ID NO:4)<br>SIQDLNVSMKLFRKQAKWKIIVKLNDGRELSLD |

Synthesized peptides used portions of human PF4 residues 22 to 54, IL-8 residues 22 to 54, and Gro-α residues 24 to 56. The C-terminal aspartic acid residue Cα carboxylate was made in the amide form. To avoid potential problems with cysteine oxidation, cysteines found in native sequences were replaced by serines. The native sequences for the PF4 (Deuel et al., *Proc. Natl. Acad. Sci USA* 74:2256–2258, 1977), IL-8 (Holt, et al. *Sem. Hematol.* 22:151–163, 1985) and GRO (Anisowicz et al., Proc. Natl. Acad. Sci. USA 84:7199–7192, 1987) peptide fragments are provided in FIG. 1.

βpep-1 was composed primarily of sequences from the α-chemokines platelet factor 4 (PF4) and interleukin-8 (IL-8). Turn/loop 1 and 2 are from PF4. Turn 2 is the PF4 peptide folding initiation site. The three strands were mostly from IL-8 with a few variations. The N-terminal dipeptide VT was included to create a potential strand 1–2 hydrophobic V25-L45 pair; a threonine was placed at position 26 to increase β-sheet propensity and to maintain solubility. IL-8 peptide K44 and E50 positions were switched to be more like PF4 with K50 and to maintain any folding stability from a potential salt-bridge pair.

The other three βpep peptides used a combination of α-chemokine sequences (primarily from strands 2 and 3 with the loop/turn initiation sequence and alternative sequences in the first turn/loop and strand 1 which were derived in part from another polypeptide from this lab. Similar β-sheet alignments found in α-chemokine polypeptides PF4, IL-8 and growth related polypeptide (Gro-α) also were generally conserved in all four peptides. βpep-2 has the IL-8 sequence I41-D54 (IIVKISDGRELSL) (SEQ ID NO:7) with the remainder of the sequence derived from the β-sheet domain of bactericidal/permeability increasing polypeptide. Three N-terminal residues 24, 26 and 28 from strand 1 were replaced with I,L,V for proper hydrophobic pairings with strand 2 residues. The number of residues in turn 1 was increased by one, thereby shifting the N-terminal numbering for paired residues by one relative to the α-chemokines.

βpep-3 differed from βpep-2 only in the first turn/loop, residues 34–39. In βpep-3, a tight turn motif containing a D-tryptophan, i.e., Y$^D$WKV (SEQ ID NO:8), from somatostatin was used. Although two cysteines (for future oxidation to cystines) were also present in βpep-3 as in somatostatin, they were maintained in the reduced state ($10^{-4}$ M perdeuterated mercaptoethanol was added to the solution). βpep4 was based on βpep-2 with residues L26, V28, M30-F33 and K38-D54 being the same. The βpep4 N-terminus (S22–S29) was taken from another α-chemokine polypeptide, neutrophil activating peptide-2 (NAP-2), and turn/loop residues 34–37 were conservative substitutions from those in βpep-2.

TABLE 2

Amino acid compositions of β-sheet-forming peptides.

|  | βpep1 (3582)[1] | βpep2 (3969)[1] | βpep3 (3839)[1] | βpep4 (3359)[1] |
|---|---|---|---|---|
| HYDROPHOBIC | | | | |
| Ile | 4 | 3 | 3 | 3 |
| Leu | 4 | 6 | 5 | 5 |
| Val | 3 | 2 | 3 | 2 |
| Ala | 2 | 1 | 1 | 1 |
| Met | — | 1 | 1 | 1 |
| Phe | 1 | 1 | 1 | 1 |
| Tyr | — | — | 1 | — |
| Trp | — | 1 | 1 | 1 |
| Pro | 2 | — | — | — |
| TOTAL HYDROPHOBIC | | | | |
|  | 16 | 15 | 16 | 14 |
| Gly | 2 | 1 | 1 | 1 |
| CHARGED | | | | |
| Asp(−) | 1 | 2 | 2 | 3 |
| Glu(−) | 1 | 2 | 2 | 1 |
| Lys(+) | 4 | 6 | 5 | 5 |
| Arg(+) | 2 | 2 | 1 | 2 |
| His(+) | 1 | 1 | — | — |
| NONCHARGED POLAR | | | | |
| Asn | 1 | 2 | 2 | 2 |
| Gln | 1 | — | — | 2 |
| Thr | 2 | — | — | — |
| Ser | 2 | 2 | 2 | 3 |
| Cys | — | — | 2 | — |
| TOTAL POLAR (charged plus noncharged) | | | | |
|  | 15 | 17 | 16 | 18 |

[1]calculated molecular weight of peptide.

EXAMPLE 2

Circular Dichroism (CD) of the β-Peptide Series

Circular dichroism (CD) is one way to measure formation of a β-sheet structure. CD spectra were measured on a JASCO JA-710 (Jasco, Eastern, Md.) automatic recording spectropolarimeter coupled with a data processor. Curves were recorded digitally and fed through the data processor for signal averaging and baseline subtraction. Spectra were recorded from 5° C. to 65° C. in the presence of 10 mM potassium phosphate, over a 185 nm to 250 nm range using a 0.5 mm path-length, thermally-jacketed quartz cuvette. Temperature was controlled by using a NesLab water bath. Peptide concentration was varied from 0.014 to 0.14 mM. The scan speed was 20 nm/min. Spectra were signal-averaged 8 times, and an equally signal-averaged solvent baseline was subtracted. These experiments are well known in the art.

For βpep-1, CD data resembled those observed for β-sheet-forming PF4 peptide. Based on CD data alone, βpep-1 appeared not to form any β-sheets. CD data for βpep-2, βpep-3 and βpep-4 showed a prominent band at 217 nm indicating formation of β-sheet structure. These three peptides were composed mostly of β-sheet structure. For βpep-4, it was surprising that the normally "random coil" 204–208 nm CD band was also prominent given NMR results, which indicated that βpep-4 formed the most stable and compact β-sheet structure of all four peptides. It may be that this band, which shifts from 204 nm to 208 nm as the 217 nm β-sheet band becomes more negative, was the result of stable turn structure.

To demonstrate that temperature modulated β-sheet folding in these βpep peptides, the molar ellipticity at 217 nm for βpep-2, βpep-3 and βpep-4 was plotted versus temperature as seen in FIG. 2. As the temperature increased from 5° C., the 217 nm band became more negative (especially for βpep-3 and βpep-4) and leveled off between 35° C. and 50° C., indicating an increase in the β-sheet population. This "cold melt" demonstrated a role for the hydrophobic effect in stabilizing β0sheet conformational populations. For βpep-2, in particular, the 217 nm band became much more positive as the temperature increased further. This effect reflected a more traditional structural "melt." For βpep-3 and βpep-4, however, temperature increases up to 65° C. showed less of an effect on the β-sheet population. These data suggested that β-sheets in βpep-3 and βpep-4 are relatively more "stable" than in βpep-2.

EXAMPLE 3

Nuclear Magnetic Resonance (NMR) of the β-Peptide Series

Figure 3:
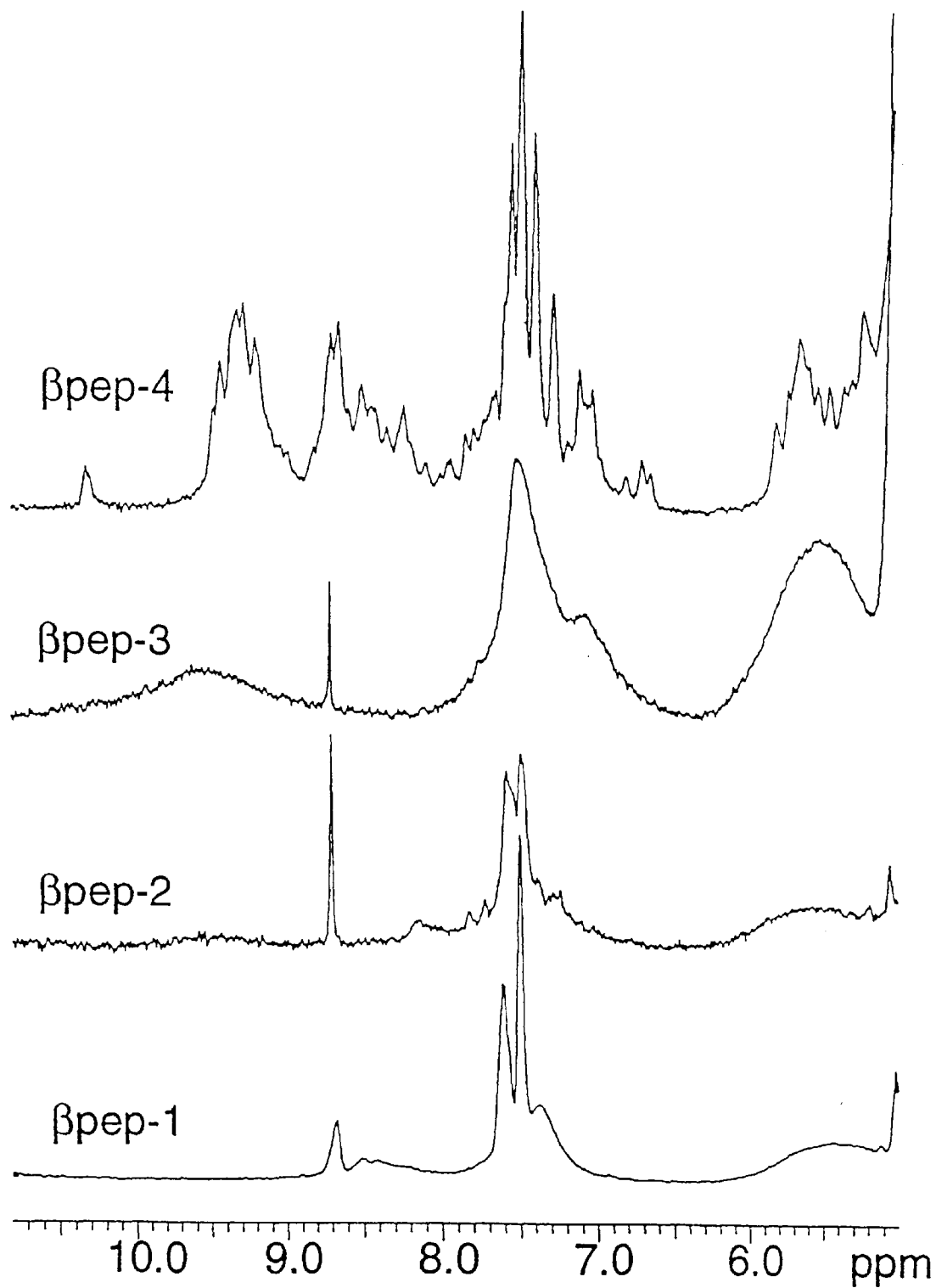
FIG. 3 is a graph depicting the $^1$HNMR spectra for βpep-1, βpep-2, βpep-3 and βpep4 in $H_2O$ at 600 MHZ. Peptide concentration was 20 mg/ml in 20 mM potassium phosphate at a temperature of 40° C. and a pH of 6.3. Spectra were accumulated with 8,000 data points over 6000 Hz sweep width and were processed with 3 Hz line broadening. Only the spectral region downfield from the HDO resonance is shown.

Since CD data indicate maximal β-sheet formation at about 40° C., NMR spectra (FIG. 3) were accumulated for all four peptides at pH 6.3, 20 mM NaCl and 40° C. For NMR measurements, freeze-dried peptide was dissolved either in $D_2O$ or in $H_2O$ /$D_2O$ (9:1). Polypeptide concentration normally was in the range of 1 to 5 mM. pH was adjusted by adding μL quantities of NaOD or DCl to the peptide sample. NMR spectra were acquired on a Bruker AMX-600 (Bruker Instrument, Inc., Bruker, Mass.) or AMX-500 NMR spectrometer. For resonance assignments, double quantum filtered COSY (Piantini et al. *J. Am. Chem. Soc.* 104:6800–6801, 1982) and 2D-homonuclear magnetization transfer (HOHAHA) spectra, obtained by spin-locking with a MLEV- 17 sequence with a mixing time of 60 ms, were used to identify spin systems (See Bax, et al. *J. Magn. Reson.* 65: 355–360, 1985). NOESY experiments (see Jeener et al., *J. Chem. Phys.* 71:4546–4553, 1979 and Wider et al. *J. Magn Reson.* 56:207–234, 1984) were performed to sequentially connect spin systems and to identify NOE connectivities. All 2D-NMR spectra were acquired in the TPPI (Marion & Wüthrich, *Biochem. Biophys. Res. Comun.* 113:967–974, 1983) or States-TPPI (States et al. *J. Magn. Reson.* 48:286–293, 1982) phase sensitive mode. The water resonance was suppressed by direct irradiation (0.8 s) at the water frequency during the relaxation delay between scans as well as during the mixing time in NOESY experiments. These experiments are well-known in the art.

2D-NMR spectra were collected as 256 to 400 t1 experiments, each with 1k or 2k complex data points over a spectral width of 6 kHz in both dimensions with the carrier placed on the water resonance. For HOHAHA (COSY) and NOESY spectra, normally 16 and 64 scans, respectively, were time averaged per t1 experiment. The data were processed directly on the Bruker AMX-600 X-32 or offline on a Bruker Aspect-1 workstation with the Bruker UXNMR program. Data sets were multiplied in both dimensions by a 30–60 degree shifted sine-bell function and zero-filled to 1k in the t1 dimension prior to Fourier transformation.

NMR data indicated that βpep-4 was best at forming a compact, triple-stranded β-sheet peptide tetramer by virtue of the presence of relatively well-defined, downfield shifted αH and NH resonances. Assuming a similar β-sheet alignment and number (13 to 16) of downfield shifted αH resonances as found in any native α-chemokine and normalizing to the aromatic resonance area (10 protons), it was estimated that this αH resonance area represents a fully folded βpep-4. Compared to betabellin 14D, NMR resonances of the β-sheet folded state for betabellin 14D were broader than would be expected for a dimer of its size, indicating formation of larger aggregates. Moreover, betabellin 14D folding was also apparently not as compact as that found in βpep-4.

NMR spectra for βpep-1, βpep-2 and βpep-3 also showed downfield shifted αH and NH resonances, which indicates β-sheet formation. While CD data suggested greater than 90% β-sheet structure for βpep-2 and βpep-3, NMR data suggested somewhat less. CD data, however, would give evidence for significant β-sheet structure even if it were highly transient in a molten globule-like or non-compact state. The presence of these downfield shifted NMR αH resonances, therefore, indicated populations of relatively well-formed β-sheet conformation which are in slow chemical exchange (600 MHZ NMR chemical shift time scale) with "non-compact" or "unfolded" conformational states whose αH protons resonate more upfield. For βpep-3, downfield shifted NHs were present in $D_2O$ for an extended period of time (4 hours), supporting the idea of some structural stability. Downfield shifted αH and NH resonances, however, were very broad with an overall envelope half-height of about 500 Hz. Although this resonance broadening could be the result of this exchange process, the possibility of intermediate exchange among similarly folded β-sheet conformations or exchange among aggregate states were also investigated.

EXAMPLE 4

Pulsed-Field gradient (PFG) NMR Self-Diffusion Measurements of the β-Peptide Series Pulsed-field gradient (PFG) NMR diffusion measurements (Gibbs, et al. *J. Magn. Reson.* 93:395–402, 1991) were performed on βpep peptides to assess self-association properties. Pulsed field gradient (PFG) NMR self-diffusion measurements were made on a Bruker AMX-600 using a GRASP gradient unit. NMR spectra for measurement of diffusion coefficients, D, were acquired using a 5 mm triple-resonance probe equipped with an actively shielded z-gradient coil. The maximum magnitude of the gradient was calibrated by using the standard manufacturer's (Bruker) procedure and was found to be 60 G/cm which is consistent with the value of 61 G/cm obtained from analysis of PFG data on water using its known diffusion constant. The PFG longitudinal eddy-current delay pulse-sequence was used for all self-diffusion measurements which were performed in $D_2O$ over the temperature range 275° K to 310° K. Peptide concentrations ranged from 3 mg/mL to 10 mg/nL.

For unrestricted diffusion of a molecule in an isotropic liquid, the PFG NMR signal amplitude normalized to the signal obtained in the absence of gradient pulses is related to D by:

$$R = \exp[-\gamma^2 g^2 \delta^2 D(\Delta - \delta/3)]$$

where γ is the gyromagnetic ratio of the observed nucleus; g and δ are the magnitude and duration of the magnetic field-gradient pulses, respectively, and Δ is the time between the gradient pulses. For these studies, experimental conditions were: δ=4 ms, g=1 to 45 G/cm, Δ=34.2 ms, and the longitudinal eddy-current delay $T_e$=100 ms. Each diffusion constant was determined from a series of 15 one dimensional PFG spectra acquired using different g values. Experimental decay curves were approximated as single exponentials.

Diffusion coefficients for peptides were calibrated by performing the same PFG NMR self-diffusion measurements on globular polypeptides lysozyme, ribonuclease and ubiquitin. Here, PFG measurements yielded D values at 20° C. of $10.1 \times 10^{-7}$ $cm^2/s$ for lysozyme, $10.2 \times 10^{-7}$ $cm^2/s$ for ribonuclease, and $14.3 \times 10^{-7}$ $cm^2/s$ for ubiquitin. These D values were within those values in the literature: $10.6 \times 10^{-7}$ $cm^2/s$ for lysozyme obtained from light scattering by extrapolation to infinite dilution; $10.7 \times 10^{-7}$ $cm^2/s$ for ribonuclease also obtained from light scattering by extrapolation to infinite dilution, and $14.9 \times 10^{-7}$ $cm^2/s$ for ubiquitin (Altieri et al., *J. Am. Chem. Soc.*, 117: 7566–7567, 1995) obtained by using similar PFG NMR measurements. This relatively good agreement in diffusion coefficients indicated that the PFG longitudinal eddy-current delay pulse sequence allows derivation of accurate diffusion constant values.

The Stokes-Einstein relationship $D=k_BT/6\pi\rho R$ was used to relate D to the macro-molecular radius, R, which was considered to be proportional to the square root of the apparent molecular weight, $M_{app}^{1/2}$ (Cantor et al. 1980. The behavior of biological macromolecules, Biophysical Chemistry, part III. New York: W. H. Freeman. pp. 979–1039). Therefore, D is proportional to $M_{app}^{-1/2}$. From these simple relationships, the ratio $D_{dimer}/D_{monomer}$ was 0.71, which is very close to 0.72 theoretically predicted for a two sphere dimer (Wills, et al. *J. Phys. Chem.* 85: 3978–3984, 1981). Use of the Stokes-Einstein relationship is specifically derived for a hard sphere, and although the actual molecular shape of each peptide aggregate would affect the diffusion coefficient, the maximum change in the ratio $D_{aggregate}/D_{monomer}$ would be about 20% in case of an improbable linear peptide tetramer. $M_{app}$ for peptides was calculated using D values of lysozyme, ribonuclease and ubiquitin as standards for monomers of known molecular weight.

Figure 4:
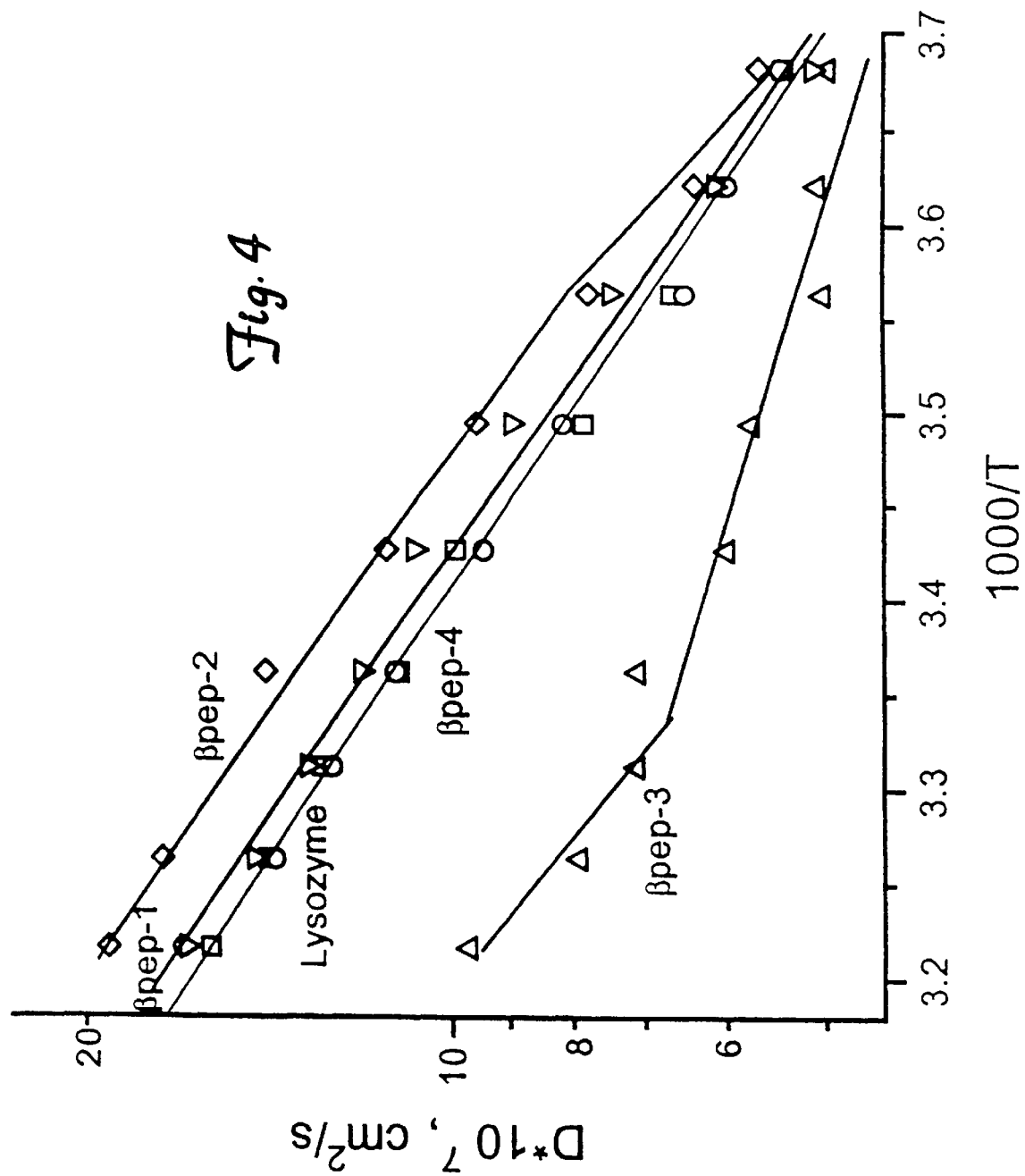
FIG. 4 is a graph showing pulsed-field gradient (PFG) NMR diffusion coefficients as a function of temperature for βpep-1, βpep-2, βpep-3, βpep4 and lysozyme.

The temperature dependence of diffusion coefficients is plotted in FIG. 4. By calibrating with diffusion data on lysozyme, ubiquitin, and ribonuclease, the average molecular weight for these peptides at 30° C. was determined: βpep-1=12,750; βpep-2=9,490; βpep-3=41,200, and βpep-4=13,700. Moreover, for βpep-1, βpep-2 and βpep-4, the temperature dependence was linear and followed the activation energy expected for the self-diffusion of water. However, the aggregate state distribution changed for βpep-2 below 10° C. and for βpep-3 over any temperature range investigated. For βpep-1 and βpep-4, the average molecular weight derived from these diffusion constants divided by the calculated monomer molecular weight (Table 1) yielded a ratio of 3.6. Since the temperature dependence of the diffusion constants was linear, the aggregate state distribution is unchanged, suggesting that a single aggregate state was present. βpep-4 showed compact β-sheet structure; βpep-1 was less clear. Given the fact that these apparent molecular weights were not being corrected for shape and electrostatic effects, the derived aggregate molecular weights can be subject to some variation. Therefore, βpep-4 may fold as a compact tetramer, and while βpep-1 also may tetrameric, there may be some distribution of monomer-dimer-tetramer.

A distribution of aggregate states was present in βpep-2 and βpep-3. The βpep-2 slope remained linear between 10° C. and 40° C. and deviated from linearity at lower temperatures. The ratio of its apparent molecular weight to its calculated monomer molecular weight (see Table 1) was 2.4 up to 10° C. and changed to 3.7 by 2° C. These data suggested that βpep-2 is on average a dimer and increased its aggregation state, probably to a tetramer, at lower temperatures. βpep-3 showed most unusual diffusion characteristics. Its aggregate state distribution continually changed with temperature. At lower temperature, its average molecular weight was that of a tetramer, while at higher temperatures, large aggregates upwards of octamers appeared to form.

EXAMPLE 5

Endotoxin Neutralizing Activity and Bactericidal Activity of βpep-1, βpep-2, βpep-3 and βpep-4

The peptides were tested for their ability to neutralize endotoxin. Quantitative endotoxin activities for these peptides were measured by Limulus amoebocyte lysate assay.

Bacteria: *P. aeruginosa* type 1 is a clinical isolate maintained in the laboratory. The isolate remains a smooth strain and was serotyped by the scheme of Homma. The Pseudomonas strain was maintained by monthly transfer on blood agar plates.

Purification of B/PI: B/PI was purified in three column-chromatography steps. In the final step, the sample was applied to a 1×180 cm molecular sieving column of Toyopearl HW55S (TosoHaas, Philadelphia Pa.) which had been equilibrated with 0.05 M glycine buffer (pH 2.5) containing 0.5M NaCl. Polypeptide concentration was determined according to Hartree (Hartree, *Analytical Biochem.*, 48:422–427 (1972)). Purity was confirmed by visualization of a SDS polyacrylamide gel following electrophoresis of 1 μg of purified BP55 polypeptide and silver staining of the gel using techniques well known in the art.

Limulus amoebocyte lysate assay: The ability of synthetic peptides to neutralize endotoxin was detected with the E-TOXATE kit manufactured by Sigma Chemicals (St. Louis, Mo.). The concentration of peptide required to completely inhibit the coagulation of Limulus amoebocyte lysate driven by 0.04 unit (or 0.01 ng) of *E. coli* O55:B5 LPS was determined by dose response and as outlined in technical bulletin No. 210 of Sigma Chemicals. Peptide or B/PI was incubated with LPS at room temperature for 5 min in 100 ul of a 1:2 dilution of pyrogen-free saline (pH 6.4). The reaction was started by addition of 100 ul of amoebocyte lysate and the final volume was 200 ul. Assuming a 10,000 molecular weight for LPS, the approximate molar ration of B/PI:LPS at neutralization was 3000 to 1.

The peptides were tested according to the method provided above. PF4 (see FIG. 1) was used as a negative control and demonstrated no endotoxin neutralizing activity. BG38L corresponds to amino acids 86–108 of B/PI and domains within B/PI have been shown to demonstrate endotoxin neutralizing acitivity. BG38L was used as a positive control in these experiments. The endotoxin neutralizing data is provided below:

| Peptide | Endotoxin Neutralizing[a] Activity |
| --- | --- |
|  | $5.0 \times 10^{-5}$ M peptide |
| βpep-1 | 70.3, n = 3 |
| βpep-2 | 100ED[c] $1.2 \times 10^{-6}$M,n = 7 |
| βpep-3 | 100ED[c] $1,2 \times 10^{-6}$ (29.5),n = 5 |
| βpep-4 | 42.8,n = 3 |
| PF4 | 0 ED[c] $5.0 \times 10^{-5}$ (23),n = 1 |
| BG38 | 34.4,n = 5 |

[a]% neutralization of 0.02U (o.2 pg of endoxtoxin from *E. coli* O55:B5)
[b]% killing of $5 \times 10^5$ *P. aeruginosa*
[c]Effective M dose (%)

This data demonstrates that the βpeptides of this invention were effective at neutralizing endotoxin activity.

All references cited herein are incorporated by reference, in their entirety, into this text. Although the invention has been described in the context of particular embodiments, it is intended that the scope of coverage of the patent be limited only by reference to the following claims.

---

What is claimed is:

1. A method for synthesizing a water-soluble β-sheet forming peptide having at least about 35% amino acids having hydrophobic side chains, the method comprising linking amino acids having charged side chains and amino acids having noncharged polar side chains with amino acids having hydrophobic side chains, wherein the amino acids having charged side chains are provided in a ratio of at least about 2:1 amino acids having positively charged side chains to amino acids having negatively charged side chains; wherein the peptide is water soluble under physiological conditions and forms β-sheet structures.

2. The method of claim 1 wherein:

(a) the water-soluble peptide has about 35% to about 55% amino acids having hydrophobic side chains; and (b) at least two of the amino acids having hydrophobic side chains are positioned in the peptide chain with an intervening turn sequence in a manner such that the two amino acids having hydrophobic side chains are capable of aligning in a pairwise fashion to form a β-sheet structure.

3. The method of claim 2 wherein the turn sequence is LXXGR (SEQ ID NO:5), wherein each X is independently selected from the group consisting of K, N, S, and D.

4. The method of claim 2 wherein the ratio of amino acids having positively charged side chains to amino acids having negatively charged side chains is no greater than about 5:1.

5. The method of claim 2 wherein the peptide includes less than about 50% amino acids having noncharged polar side chains.

6. The method of claim 2 wherein the peptide includes less than about 20% amino acids having noncharged polar side chains.

7. The method of claim 2 wherein the hydrophobic side chains are aliphatic or aromatic.

8. The method of claim 2 wherein the peptide includes about 40% to about 50% amino acids having hydrophobic side chains.

9. The method of claim 2 wherein at least three of the amino acids having hydrophobic side chains are positioned in the peptide with two intervening turn sequences in a manner such that the three amino acids having hydrophobic side chains are capable of aligning to form a β-sheet structure.

10. The method of claim 2 wherein there are at least three intervening amino acids between the two amino acids having hydrophobic side chains.

11. The method of claim 10 wherein there are no greater than about 16 amino acids between the two amino acids having hydrophobic side chains.

12. The method of claim 10 wherein the intervening amino acids have hydrophobic side chains, charged side chains, or noncharged polar side chains.

13. The method of claim 2 wherein the amino acids are spacially positioned in the folded peptide to form a substantially hydrophobic surface.

14. The method of claim 13 wherein the amino acids are spacially positioned in the folded peptide such that one peptide molecule is capable of self-associating with another peptide molecule to form a multimer.

15. A method for synthesizing a water-soluble β-sheet forming peptide having at least about 35% amino acids having hydrophobic side chains, the method comprising linking amino acids having charged side chains and less than about 20% amino acids having noncharged polar side chains with amino acids having hydrophobic side chains, wherein the peptide is water soluble under physiological conditions and forms β-sheet structures, and further wherein:

(a) the amino acids having charged side chains are provided in a ratio of at least about 2:1 amino acids having positively charged side chains to amino acids having negatively charged side chains;

(b) the water soluble peptide has about 35% to about 55% amino acids having hydrophobic side chains;

(c) at least two of the amino acids having hydrophobic side chains are positioned in the peptide with an intervening turn sequence in a manner such that the two amino acids having hydrophobic side chains are capable of aligning in a pairwise fashion to form a β-sheet structure; and (d) the turn sequence is LXXGR (SEQ ID NO:5), wherein each X is independently selected from the group consisting of K, N, S, and D.

* * * * *